(12) United States Patent
Hijikata et al.

(10) Patent No.: US 11,647,894 B2
(45) Date of Patent: May 16, 2023

(54) PROCESSOR FOR ENDOSCOPE AND ENDOSCOPIC SYSTEM

(71) Applicant: HOYA CORPORATION, Tokyo (JP)

(72) Inventors: Takao Hijikata, Tokyo (JP); Yuya Masukawa, Tokyo (JP); Toru Mukumoto, Tokyo (JP); Motoharu Endo, Tokyo (JP)

(73) Assignee: HOYA CORPORATION, Tokyo (JP)

(*) Notice: Subject to any disclaimer, the term of this patent is extended or adjusted under 35 U.S.C. 154(b) by 0 days.

(21) Appl. No.: 17/256,901

(22) PCT Filed: Feb. 26, 2020

(86) PCT No.: PCT/JP2020/007864
§ 371 (c)(1),
(2) Date: Dec. 29, 2020

(87) PCT Pub. No.: WO2020/175585
PCT Pub. Date: Sep. 3, 2020

(65) Prior Publication Data
US 2021/0378488 A1 Dec. 9, 2021

(30) Foreign Application Priority Data

Feb. 27, 2019 (JP) .............................. JP2019-033543

(51) Int. Cl.
A61B 1/04 (2006.01)
A61B 1/06 (2006.01)
A61B 1/00 (2006.01)

(52) U.S. Cl.
CPC ...... A61B 1/00121 (2013.01); A61B 1/00013 (2013.01); A61B 1/00045 (2013.01);
(Continued)

(58) Field of Classification Search
CPC ............ A61B 1/00121; A61B 1/00013; A61B 1/00045; A61B 1/00124; A61B 1/0661;
(Continued)

(56) References Cited

U.S. PATENT DOCUMENTS 5,509,096 A * 4/1996 Easley ................. G02B 6/4298
385/88
2002/0098732 A1* 7/2002 Shimizu ............. A61B 1/00128
439/352
(Continued)

FOREIGN PATENT DOCUMENTS

EP 2 949 260 A1 12/2015
JP H11-178789 A 7/1999
(Continued)

OTHER PUBLICATIONS

International Search Report (ISR) dated Apr. 14, 2020 filed in PCT/JP2020/007864.
Examination Report issued by the German Patent and Trademark Office for corresponding German patent application No. 11 2020 000 065.6, dated Mar. 8, 2023.

Primary Examiner — John P Leubecker
Assistant Examiner — Li-Ting Song
(74) Attorney, Agent, or Firm — Greenblum & Bernstein, P.L.C.

(57) ABSTRACT

One of two connector receiving parts of a processor for endoscope has a shutter mechanism configured to open a shutter by an external force, the shutter having a gap through which a connector-side connection end section passes, and being configured to partition a recessed space of the connector receiving part with respect to an outside. In addition, the processor for endoscope includes a lock mechanism configured to make the shutter into the locked state during a period when another connection end section on the connector side and a processor-side connection end section are
(Continued)

connected, and release the locked state of the shutter when the connection between the other connection end section on the connector side and the processor-side connection end section is released.

12 Claims, 5 Drawing Sheets

(52) U.S. Cl.
CPC .......... *A61B 1/00124* (2013.01); *A61B 1/04* (2013.01); *A61B 1/00114* (2013.01); *A61B 1/00117* (2013.01); *A61B 1/00126* (2013.01); *A61B 1/00128* (2013.01); *A61B 1/0661* (2013.01)

(58) Field of Classification Search
CPC .......... A61B 1/00126; A61B 1/00128; A61B 1/00114; A61B 1/00117; A61B 1/04
See application file for complete search history.

(56) References Cited

U.S. PATENT DOCUMENTS

| | | | |
|---|---|---|---|
| 2008/0086030 A1* | 4/2008 | Itoi | A61B 8/4433 600/132 |
| 2008/0232746 A1* | 9/2008 | Frith | G02B 6/4298 385/88 |
| 2016/0007843 A1 | 1/2016 | Nakajima | |
| 2017/0254964 A1* | 9/2017 | Yajima | G02B 6/3878 |
| 2018/0263464 A1 | 9/2018 | Lohier et al. | |

FOREIGN PATENT DOCUMENTS

| | | |
|---|---|---|
| JP | 2006-181148 A | 7/2006 |
| JP | 2007-29160 A | 2/2007 |
| JP | 2008-229204 A | 10/2008 |
| JP | 2019-58309 A | 4/2019 |
| JP | 2019-76655 A | 5/2019 |
| WO | 2015/045463 A1 | 4/2015 |

* cited by examiner

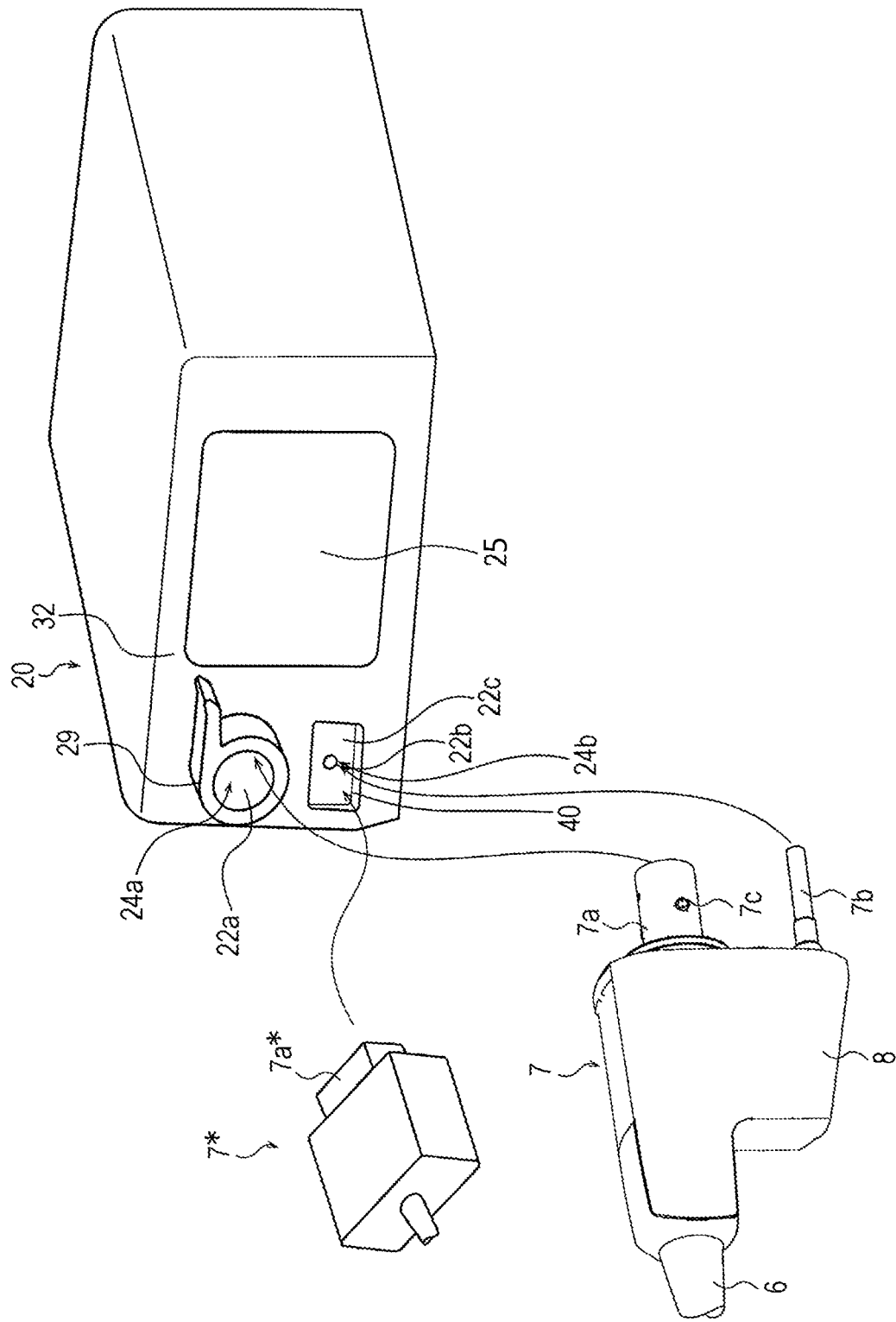

PROCESSOR FOR ENDOSCOPE AND ENDOSCOPIC SYSTEM

TECHNICAL FIELD

The present invention relates to a processor for endoscope configured to connect to an endoscope connector and an endoscopic system.

BACKGROUND ART

An endoscopic system is used to observe or treat a living tissue inside a human body. The endoscopic system includes an endoscope that captures an image of a living tissue with an image sensor and transmits the captured image to a processor for endoscope (hereinafter simply referred to as a processor), and a processor that processes a signal of the captured image to create an image for display. The endoscope is provided with a connector for connecting to the processor. On the other hand, the processor includes a connector receiving part that is provided with a recessed space for connector insertion for receiving an electrical connection terminal on an endoscope-side connector and connecting to an electrical connection terminal on a processor side.

For example, there is known an electronic endoscope device that closes an insertion port of an unused connector receiving part to prevent moisture or the like from penetrating into the connector receiving part and ensures electrical safety (Patent Literature 1).

CITATION LIST

Patent Literature

Patent Literature 1: JP 2008-229204 A

SUMMARY OF INVENTION

Technical Problem

In the above electronic endoscope device, a movable shield body that sets the connector receiving part to an exposed state and a closed state is provided, and when the connector receiving part corresponding to a connector of an electronic scope to be used is exposed by the movable shield body, a connector receiving part opening/closing mechanism that operates to close another connector receiving part is provided. The movable shield body can close the insertion port of the connector receiving part that is not in use to prevent moisture from penetrating into the connector receiving part and ensure the electrical safety and the like.

In the above electronic endoscope device, only one of the two connector receiving parts, which are the exposed or closed state, is used regardless of which type of endoscope is connected. On the other hand, in the processor connected to the endoscope of the type that uses two connector receiving parts at the same time, it is considered that there is a gap between the connector receiving part and the inserted connector in one connector receiving part. This is because each recessed space of the connector receiving part is formed to receive the corresponding endoscope connector. For example, when an operator's finger enters such a gap while the processor is in use, there is a risk of touching the inside of the hot connector receiving part. In addition, since the finger enters the gap, static electricity accumulated in the processor may be discharged and the processor may be damaged.

An object of the present invention is to provide a processor for endoscope capable of preventing a user's finger or the like from entering a gap formed between an endoscope connector and a connector receiving part in the processor for endoscope to which an endoscope using a plurality of connector receiving parts at the same time is connected, and an endoscopic system.

Solution to Problem

According to one aspect of the present invention, a processor for endoscope includes:

a first connector receiving part configured to be provided with a first recessed space for receiving a connector-side first connection end section of the connector-side first connection end section and a connector-side second connection end section of an endoscope connector connected to the processor for endoscope, and connect the connector-side first connection end section received in the first recessed space and a processor-side first connection end section of the processor for endoscope;

a second connector receiving part configured to be provided with a second recessed space different from the first recessed space, and connect the connector-side second connection end section received in the second recessed space and a processor-side second connection end section of the processor for endoscope;

a shutter mechanism configured to be provided in the second connector receiving part and open a shutter by an external force, the shutter having a gap through which the connector-side second connection end section passes and being configured to partition the second recessed space from the outside; and a lock mechanism configured to make the shutter into a locked state constraining the shutter from an openable/closable operation state to a closed state during a period when the connector-side first connection end section and the processor-side first connection end section are connected, and release the locked state of the shutter when the connection between the connector-side first connection end section and the processor-side first connection end section is released.

It is preferable that the shutter be configured to be opened to the outside by moving in the second recessed space, and the lock mechanism have a stopper of which at least a part freely enters and exits a path in the second recessed space in which the shutter moves, and be configured so that the at least a part of the stopper enters the path to prevent the shutter from moving.

The processor for endoscope further includes a guiding mechanism configured to guide the connector-side first connection end section to a connection position with the processor-side first connection end section while receiving the connector-side first connection end section, in which the lock mechanism is preferably configured so that the at least a part of the stopper enters the path in conjunction with an operation of the guiding mechanism at guides the connector-side first connection end section.

The processor for endoscope further includes an operation lever configured to guide the connector-side first connection end section to the connection position with the processor-side first connection end section while receiving the connector-side first connection end section, in which the lock mechanism is preferably configured so that the at least a part of the stopper enters the path in conjunction with an operation of the operation lever that guides the connector-side first connection end section.

The processor for endoscope further includes a guiding mechanism configured to guide the connector-side first connection end section to a connection position with the processor-side first connection end section while receiving the connector-side first connection end section, in which the lock mechanism is preferably configured so that the shutter is in the locked state in conjunction with an operation of the guiding mechanism that guides the connector-side first connection end section.

The processor for endoscope is preferable in an aspect in which the second connector receiving part is configured to connect the connector-side second connection end section and the processor-side second connection end section so as to enable transmission and reception of light, and the transmission and reception of light is performed by spatial transmission via an optical path in a space between the connector-side second connection end section and the processor-side second connection end section.

The first connector receiving part may be configured to connect the connector-side first connection end section and the processor-side first connection end section so as to enable communication and transmission and reception of power, and the communication and the transmission and reception of power may be performed by the spatial transmission of light via the optical path in the space between the connector-side first connection end section and the processor-side first connection end section.

According to another aspect of the present invention, an endoscopic system includes:

the processor for endoscope; and an endoscope having the connector.

The endoscopic system is preferable in an aspect in which when the connector is referred to as a first connector and the connector-side first connection end section is referred to as a first connector-side first connection end section, the second connector receiving part is configured to receive a second connector-side first connection end section of a second connector mounted on the second connector receiving part and different from the first connector in the second recessed space, and connect the received second connector-side first connection end section and the processor-side third connection end section of the processor for endoscope.

According to still another aspect of the present invention, an endoscopic system includes:

the processor for endoscope;

an endoscope having a second connector mounted on the second connector receiving part and different from the first connector when the connector is referred to as a first connector; and a cover member covering the first recessed space.

The processor for endoscope is preferable in an aspect in which the second connector receiving part is configured to receive the second connector-side first connection end section of the second connector in the second recessed space and connect the received second connector-side first connection end section and a processor-side third connection end section of the processor for endoscope.

The processor for endoscope is preferable in an aspect in which a recessed space, that receives a light incident end section, of each of the first connector and the second connector commonly including the light incident end section as the connector-side second connection end section, the light incident end section receiving incidence of light from the processor for endoscope, is provided in the second recessed space.

Advantageous Effects of Invention

According to the processor for endoscope and the endoscopic system described above, in the processor for endoscope to which the endoscope using the plurality of connector receiving parts at the same time is connected, it is possible to prevent the user's finger from entering the space between the endoscope connector and the connector receiving part.

BRIEF DESCRIPTION OF DRAWINGS

FIG. 2 is an enlarged perspective view illustrating an example of a connector and a processor according to an embodiment.

DESCRIPTION OF EMBODIMENTS

Figure 1:
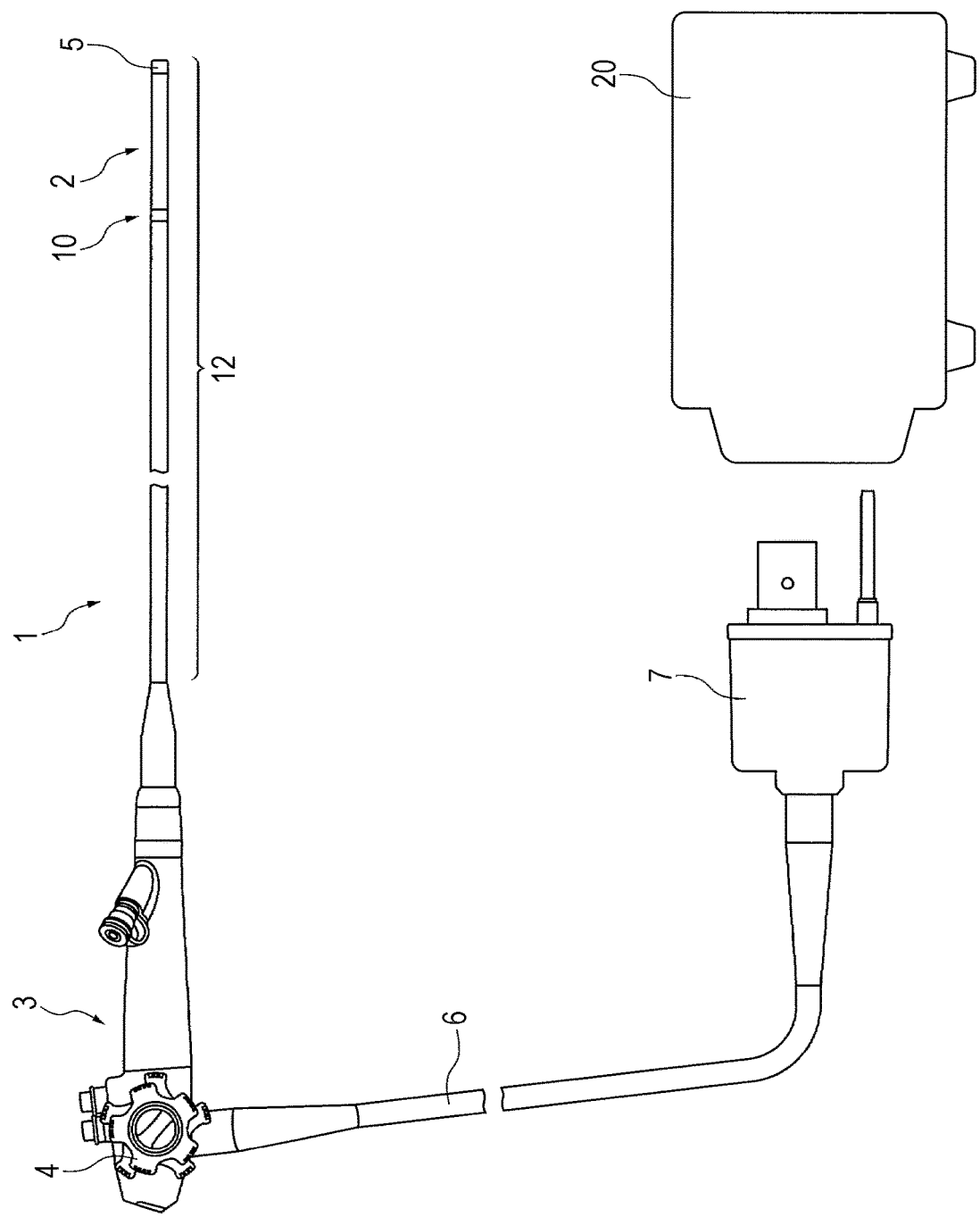
FIG. 1 is an external perspective view of an endoscope for medical use according to an embodiment.

Hereinafter, a processor for endoscope and an endoscopic system according to an embodiment will be described with reference to the drawings. FIG. 1 is an external perspective view of an electronic endoscope for medical use (hereinafter, simply referred to as an endoscope) and a processor according to an embodiment. In a front-back direction in the following explanation, a distal tip side of a flexible tube 1 of the endoscope is defined as "front", and a distal tip side (connector 7 side) of a universal tube 6 is defined as "back".

The endoscope for medical use includes an operation unit 3, a flexible tube 1 extending forward from an operation unit 3 and having flexibility, a bending tube 2 connected to the front of the flexible tube 1 via a connection portion 10, a universal tube 6 extending rearward from the operation unit 3, and a connector 7 fixed to a rear end of the universal tube 6. A plurality of bending operation wires are inserted into the operation unit 3, the flexible tube 1, and the bending tube 2, and each bending operation wire has a distal tip connected to a rear end of a distal tip 5, in which the rear end is connected to a bending operation lever 4 (bending operation mechanism) of the operation unit 3 via the bending operation wire. The bending tube 2 is bent in any direction and at any angle according to the operation of the bending operation lever 4.

The distal tip of the bending tube 2 is provided with the distal tip 5. The distal tip 5 is made of a hard resin material that cannot substantially be deformed elastically, and a distal tip surface consisting of a flat surface of the distal tip 5 is provided with an aperture with an objective lens (observation lens), an outlet provided with an illumination lens, an air supply/water supply port, a forceps port, and the like.

A light guide fiber (not illustrated) whose front end is connected to the illumination lens is provided inside the operation unit 3, the flexible tube 1, the bending tube 2, the universal tube 6, and the connector 7. Further, an image sensor (not illustrated) located immediately after the objective lens is provided inside the distal tip 5.

The flexible tube 1, the bending tube 2, the distal tip 5, and the connection portion 10 form the insertion portion 12 that is inserted into the body cavity. A cable for an image signal extending from the image sensor provided at the distal tip 5 extends to the inside of the connector 7 through the inside of the bending tube 2, the flexible tube 1, the operation unit 3, and the universal tube 6. The connector 7 is connected to the processor for endoscope (hereinafter simply referred to as a processor) 20. The processor 20 processes the image signal transmitted from the image sensor and controls an image of a subject captured by the image sensor to be displayed on a monitor (not illustrated). The processor 20 includes a light source device (not illustrated) that emits light that serves as illumination light for illuminating a living tissue. The light emitted from the light source device is transmitted in a light carrying bundle (LCB) cable to the distal tip 5 via the connector 7. This LCB cable is provided in the universal tube 6 and the flexible tube 1.

Since the endoscope including the connector 7 is cleaned and disinfected to be reusable, the connector 7 has high watertightness and airtightness, and an internal structure of the connector 7 is in a closed state. For this reason, a housing that keeps the internal structure closed is provided on the outside of the connector 7. The housing and the part covered by the housing are called a connector main body part 8.

As an internal structure, the connector 7 includes a signal processing circuit that processes a signal before transmitting, to the processor 20, an image signal transmitted from the image sensor to the processor 20, and a memory that records unique information of the endoscope. The unique information of the endoscope includes, for example, the number of pixels or sensitivity of the image sensor, a frame rate that can be operated, a model number, and the like. The signal processing circuit outputs the unique information read from the memory to a system controller (not illustrated) provided in the processor 20.

That is, the endoscope has an image sensor for capturing an image of the living tissue provided at the distal tip thereof, the insertion portion 12 inserted into the body cavity, and the connector 7 provided so as to be connectable to the processor 20. The connector 7 includes a signal processing circuit which is an electronic circuit that processes the signal of the captured image transmitted from the image sensor, and has a function of transmitting, to the processor 20, the signal of the captured image which is subjected to signal processing.

FIG. 2 is an enlarged perspective view illustrating an example of connectors 7 and 7\* and the processor 20. FIGS. 3(*a*) and 3(*b*) are diagrams for explaining a state in which the processor 20 and the connectors 7 and 7\* according to an embodiment are connected.

The connector 7 (first connector) includes an electrical connection end section 7*a* (connector-side first connection end section) and a light incident end section 7*b* (connector-side second connection end section) in addition to the connector main body part 8. The electrical connection end section 7*a* has a tubular shape with an open distal tip and protrudes from the connector main body part 8. An electrical connection terminal (not illustrated) that is connected to a signal line extending from the image sensor, a control line controlling the operation of the image sensor and the like, or a transmission line transmitting power supplied from the processor 20 is provided inside the electrical connection end section 7*a* surrounded in a tubular shape.

The light incident end section 7*b* has a tubular shape with an open distal tip and protrudes from the connector main body part 8. The LCB cable that transmits the illumination light emitted from the light source device in the processor 20 to the distal tip 5 is provided inside the light incident end section 7*b* surrounded in a tubular shape. An opening of the light incident end section 7*b* is provided with an opening surface through which the LCB cable receives the incident illumination light.

Each of the electrical connection end section 7*a* and the light incident end section 7*b* is connected to the connector receiving part 22*a* and the optical connector receiving part 22*b* on the processor 20 side, which will be described later.

The processor 20 includes a connector receiving parts 22*a* and 22*c*, an optical connector receiving part 22*b*, and an operation panel 25.

The operation panel 25 is a panel for inputting an instruction for the processor 20 and the endoscope to operate in response to the observation or examination that an operator wants to perform with the endoscopic system. The instruction input includes, for example, switching between modes such as a normal observation mode or a special observation mode, processing contents for applying a living tissue to the captured image acquired by the image sensor, or an instruction input of a display form for displaying the image or inspection result on a monitor (not illustrated).

The connector receiving part 22*a* (first connector receiving part) and the optical connector receiving part 22*b* are parts that receive the electrical connection end section 7*a* and the light incident end section 7*b* illustrated in FIG. 2, respectively, and has a recessed space for connector insertion 24*a* (first recessed space) and a recessed space for optical connector insertion 24*b*.

The back part of the recessed space for connector insertion 24*a* is provided with an electrical connection terminal 28*a* on a processor side (processor-side first connection end section) (see FIGS. 3(*a*) and 3(*b*)), and the back part in the recessed space for optical connector insertion 24*b* is provided with the light emission part 28*b* (processor-side second connection end section) of the illumination light of the light source device. Therefore, the connector 7 is moved to the processor 20 side from the state illustrated in FIG. 3(*a*), and each of the electrical connection end section 7*a* and the light incident end section 7*b* of the connector 7 is inserted into a predetermined position (connection position) of the recessed space for connector insertion 24*a* and the recessed space for optical connector insertion 24*b*, and as a result, the connector-side electrical connection terminal and the electrical connection terminal 28*a* on the processor side are connected, and an open end of the LCB cable is located at an opposite position of the light emission part 28*b* of the illumination light. As a result, the communication and the transmission and reception of power can be performed between the electrical connection end section 7*a* and the electrical connection terminal 28*a*, and the transmission and reception of the illumination light can be performed between the light incident end section 7*b* and the light emission part 28*b*. The transmission and reception of the illumination light is performed by spatial transmission via an optical path in a space between connection end sections connected to each other (located opposite to each other).

That is, the processor 20 includes the connector receiving part 22*a* that receives the electrical connection terminal of the endoscope-side connector 7 and is provided with the recessed space for connector insertion 24*a* for connecting to the electrical connection terminal 28*a* on the processor 20 side, and the optical connector receiving part 22*b* that receives the light incident end section 7b of the endoscope-side connector 7 and is provided with the recessed space for optical connector insertion 24b for arranging the open end of the LCB cable at the opposite position (connection position) of the light emission part 28b of the light source device on the processor 20 side. Note that in this specification, the connection between the endoscope-side connection end section and the processor-side connection end section means a connection that allows the communication or the transmission and reception of power or light between both connection end sections. The connection end sections connected to each other may be physically in contact with each other, or may be arranged apart with a space therebetween. The communication and the transmission and reception of power between the two connection end sections are performed by wire or wirelessly.

Figure 3A:
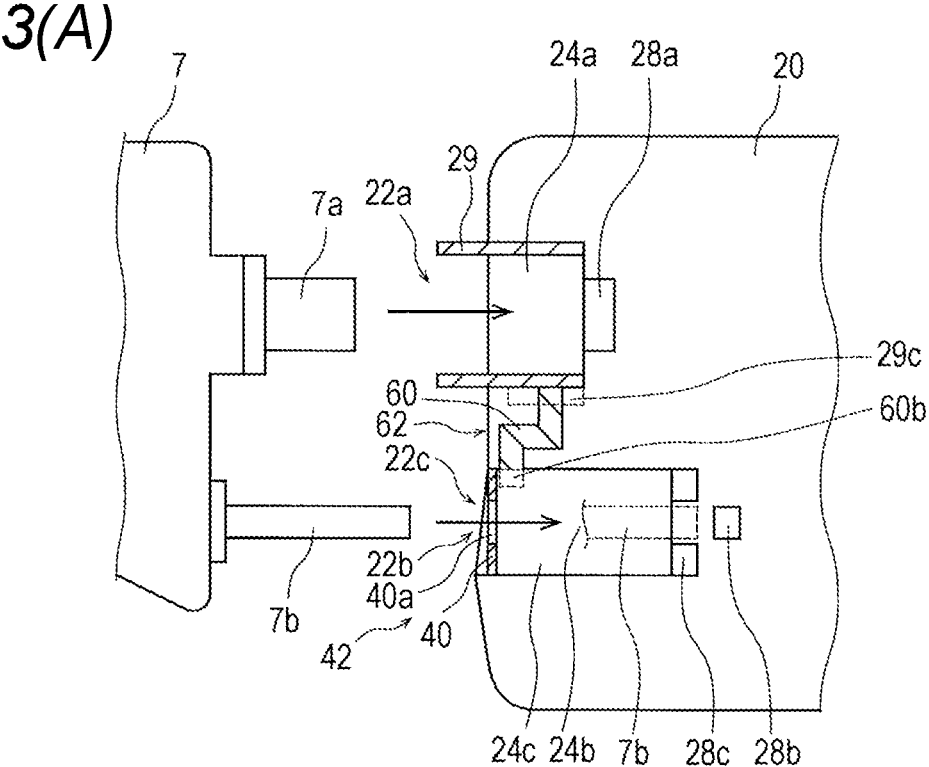
FIGS. 3(A) and 3(B) are diagrams illustrating a processor and two connectors according to an embodiment.
Figure 3B:
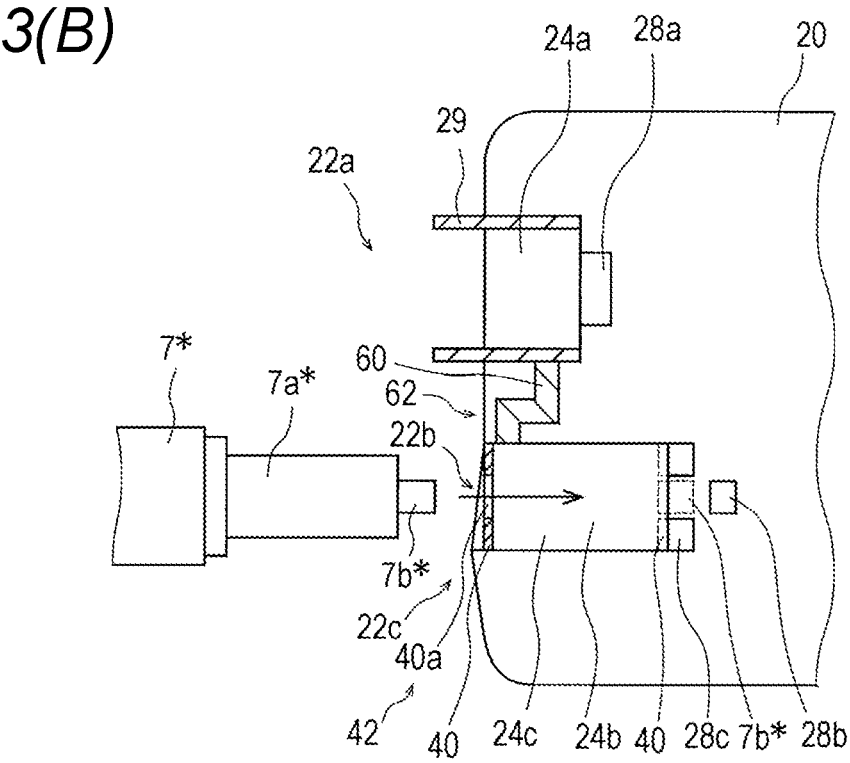

In addition, as illustrated in FIG. 2, the processor 20 includes the connector receiving part 22c that receives an electrical connection terminal of another type of endoscope-side connector 7* and is provided with a recessed space for connector insertion 24c (second recessed space) for connecting to the electrical connection terminal 28c on the processor 20 side (processor-side third connection end section) (see FIGS. 3(a) and 3(b)). The connector receiving part 22c is integrated with the optical connector receiving part 22b to form the second connector receiving part. When the connector 7* is connected to the connector receiving part 22c, the optical connector receiving part 22b receives a light incident end section 7b* (see FIG. 3(b)) in the recessed space for optical connector insertion 24b and arranges the open end of the LCB cable at the opposite position of the light emission part 28b of the light source device on the processor 20 side. Therefore, when the connectors 7 and 7* are connected to the processor 20, the light incident end section 7b and the light incident end section 7b* are configured to be inserted into the recessed space for optical connector insertion 24b, sharing the optical connector receiving part 22b. Therefore, as compared with the processor in which the optical connector receiving part is provided separately from other connector receiving parts, the space in the processor 20 is less restricted, and for example, a large arrangement space can be secured for parts such as a monitor. In addition, the processor 20 can be miniaturized.

In this way, the processor 20 includes the connector receiving part 22a that receives the electrical connection end section 7a of the connector 7 and is provided with the recessed space for connector insertion 24a for connecting to the electrical connection terminal 28a on the processor 20 side, and the connector receiving part 22c that receives an electrical connection end section 7a* of the connector 7* (second connector-side first connection end section) (see FIG. 3(b)) and is provided with the recessed space for connector insertion 24c for connecting to the electrical connection terminal 28c on the processor 20 side. In addition, the recessed space for optical connector insertion 24b is located at an opposite position of the light emission part 28b of the illumination light on the processor 20 side, receiving the light incident end section 7b of the connector 7 and the light incident end section 7b* of the connector 7*. As a result, it is possible to transmit and receive the illumination light between the light incident end section 7b or the light incident end section 7b* and the light emission part 28b. FIG. 3(a) illustrates the position of the light incident end section 7b at the connection position by a broken line, and FIG. 3(b) illustrates the position of light incident end section 7b* at the connection position by a broken line. In this way, the optical connector receiving part 22b and the recessed space for optical connector insertion 24b are used both when connecting the connector 7 to the processor 20 and when connecting the connector 7* to the processor 20. As described above, the processor 20 includes two connector receiving parts 22a and 22c provided with the recessed spaces for connector insertion 24a and 24c.

The electrical connection end section 7a of the connector 7 has a cylindrical shape, and the electrical connection end section 7a* of the connector 7 * has a rectangular shape. As illustrated in FIGS. 2 and 3(b), the recessed space for optical connector insertion 24b of the optical connector receiving part 22b is provided in the recessed space for connector insertion 24c into which the electrical connection end section 7a* of the connector 7* is inserted. That is, the recessed space for optical connector insertion 24b shares a part of the space of the recessed space for connector insertion 24c with the recessed space for connector insertion 24c.

The connector receiving part 22c is provided with a shutter mechanism 42. The shutter mechanism 42 has a shutter 40 that partitions the recessed space for connector insertion 24c from the outside. By the partition from the outside by the shutter 40, liquids such as water are prevented from penetrating into the recessed space for connector insertion 24c, and the electrical safety is ensured. The shutter 40 has a gap 40a through which the light incident end sections 7b and 7b* of the connectors 7 and 7* pass. In FIGS. 3(a) and 3(b), the shutter 40 is a plate-shaped member, and as illustrated in FIGS. 2 to 5, the shutter 40 has a gap 40a of a circular hole corresponding to the shape of the light incident end section 7b. Therefore, when the connector 7 is connected to the processor 20, the shutter 40 can pass the light incident end section 7b while partitioning the recessed space for connector insertion 24c with respect to the outside.

In addition, the shutter mechanism 42 is configured so that the shutter 40 can be opened by an external force. Specifically, the shutter 40 is configured to open outward by moving within the recessed space for connector insertion 24c. In FIG. 3(b), the shutter 40 is urged on an inlet side of the recessed space for connector insertion 24c by an urging member such as a spring, and is applied with an external force to be able to move (slide) to a back side within the recessed space for connector insertion 24c. When the connector 7* is connected to the processor 20, the shutter 40 is pushed by the connector 7* and moves to the back side within the recessed space for connector insertion 24c to open the recessed space for connector insertion 24c and receive the electrical connection end section 7a* of the connector 7* The shutter 40 is configured to move within the recessed space for connector insertion 24c while maintaining a posture in a direction vertical to a horizontal direction. In FIG. 3(b), the shutter 40 pushed to the back side by the connector 7* is shown by a broken line.

The shutter 40 is constrained from the openable and closable operation state to the closed state during the period when the electrical connection end section 7a of the connector 7 and the electrical connection terminal 28a on the processor 20 side are connected by the lock mechanism 62 to be described later, and is configured to be in the locked state. On the other hand, the shutter 40 is configured so that the locked state is released when the connection between the electrical connection end section 7a and the electrical connection terminal 28a is released by the lock mechanism 62. In FIGS. 3(a) and 3(b), the shutter 40 is constrained to a closed state at an end section of the inlet side of the recessed space for connector insertion 24c. The shutter 40 can move by being applied with the external force in the operable state, but does not move by being applied with the external force in the closed state.

The processor 20 has a lock mechanism 62. As described above, since the recessed space for connector insertion 24c of the connector receiving part 22c is configured to receive the electrical connection end section 7a* of the connector 7*, when the light incident end section 7b of the connector 7 is inserted into the recessed space for optical connector insertion 24b to connect the connector 7 to the processor 20, the portion of the recessed space for connector insertion 24c that surrounds the light incident end section 7b becomes a gap. Therefore, when the shutter can be operated to be opened and closed, for example, the operator's finger may touch the shutter and push and open the shutter. For this reason, the operator's finger may get into the gap between the light incident end section 7b and the connector receiving part 22c, and may touch the light emission part 28b on the back side or the portion of the connector receiving part 22c in the vicinity thereof. Since these portions become hot during the use of the processor 20, it is dangerous for the user's finger to touch theses portions. This can also happen even when the connector 7 is removed to replace the endoscope. Also, the operator's finger gets into the gap between the light incident end section 7b and the connector receiving part 22c, and therefore, the static electricity accumulated in the processor is discharged from the electrical connection terminal 28c exposed in the gap, and the processor may be damaged. According to the processor 20 described above, since the shutter 40 is constrained to the closed state while the electrical connection end section 7a and the electrical connection terminal 28a are connected, that is, while the connector 7 is connected to the processor 20, even when the shutter 40 is pressed by the operator's finger, the shutter 40 does not open to prevent the operator's finger from getting into the gap between the light incident end section 7b and the connector receiving part 22c.

According to the processor 20 described above, when the connection between the electrical connection end section 7a and the electrical connection terminal 28a is released, that is, when the connection between the connector 7 and the processor 20 is released, the locked state of the shutter 40 is released. Therefore, when connecting the connector 7* to the processor 20, the electrical connection end section 7a* of the connector 7* can be pushed to push and open the shutter 40 and can be inserted into the recessed space for connector insertion 24c. When the electrical connection end section 7a and the electrical connection terminal 28a are released, the light incident end section 7b and the light emission part 28b are also released. The connection between the connector 7 and the processor 20 is released since each of the electrical connection end section 7a and light incident end section 7b is separated from the connection position in the connector receiving part 22a and the recessed space for optical connector insertion 24b.

As described above, when the shutter 40 is configured to open outward by moving within the recessed space for connector insertion 24c, according to an embodiment, the lock mechanism 62 has a stopper 60 and it is preferable that at least a part of the stopper 60 be configured to enter the movement path of the shutter 40 and prevent the shutter 40 from moving. As illustrated by the broken line in FIG. 3(a), the stopper 60 is configured so that at least a part of the stopper 60 can freely enter and exit the movement path in the recessed space for connector insertion 24c where the shutter 40 moves. The movement path means the space in the recessed space for connector insertion 24c where the shutter 40 can be located, and in the illustrated example, means substantially the entire space in the recessed space for connector insertion 24c except the recessed space for optical connector insertion 24b. In the example illustrated in FIGS. 3(a) and 3(b), a lower end section 60b of the stopper 60 entering and exiting the movement path in the recessed space for connector insertion 24c is located at the back side of the recessed space for connector insertion 24c with respect to the shutter 40 which is in the closed state. Therefore, the lower end section 60b of the stopper 60 enters the recessed space for connector insertion 24c, and the shutter 40 comes into contact with the stopper 60 from the inlet side of the recessed space for connector insertion 24c, so the shutter 40 is prevented from moving. The stopper 60 is configured to enter the recessed space for connector insertion 24c in conjunction with the operation of the guiding mechanism 26 and the operation lever 29 to be described later, for example. In FIGS. 3(a) and 3(b), the processor 20 is indicated by a cut surface passing through the recessed spaces 24a to 24c.

According to one embodiment, the processor 20 includes the guiding mechanism 26 configured to guide the endoscope-side electrical connection end section 7a to the connection position with the electrical connection terminal 28a on the processor 20 side while receiving the electrical connection end section 7a. Specifically, the guiding mechanism 26 grips the electrical connection end section 7a inserted into a predetermined position in the recessed space for connector insertion 24a by locking the electrical connection end section 7a to a part of the guiding mechanism 26, and guides the electrical connection end section 7a to the position of electrical connection terminal 28a provided in the back of recessed space for connector insertion 24a.

Figure 4:
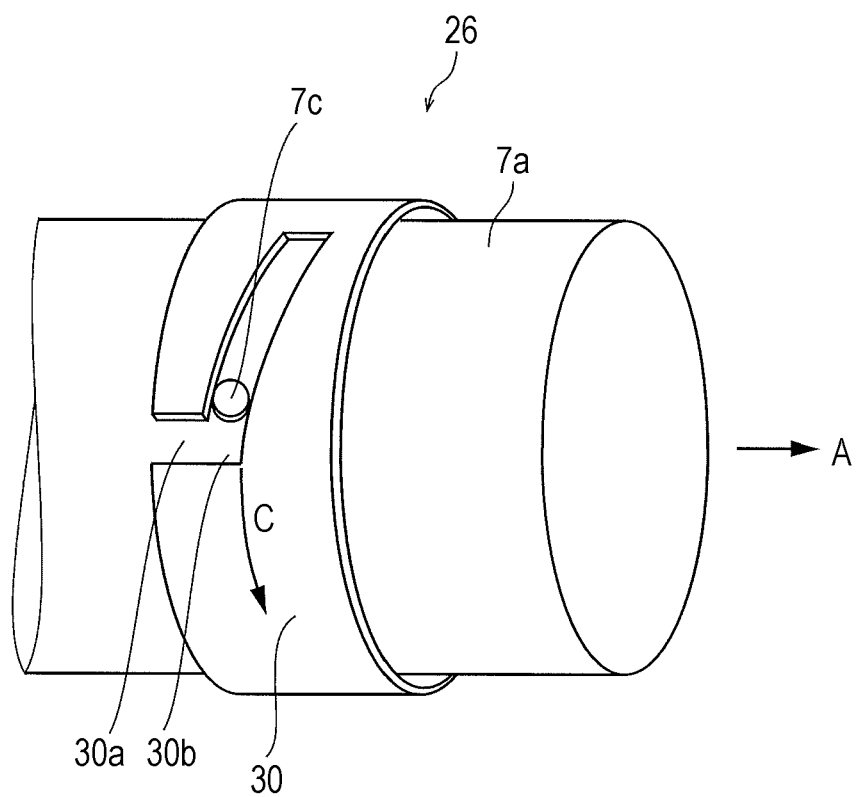
FIG. 4 is a diagram schematically illustrating an example of a guiding mechanism according to an embodiment.

Here, the guiding mechanism 26 will be described with reference to FIG. 4. FIG. 4 is a diagram schematically illustrating an example of the guiding mechanism 26. The guiding mechanism 26 includes a cylindrical tube member 30 with open both ends. The cylindrical tube member 30 is configured so that the electrical connection end section 7a can be inserted into the tube of the cylindrical tube member 30. A surface (outer peripheral side surface) of the electrical connection end section 7a to be inserted is provided with a protrusion 7c, whereas the cylindrical tube member 30 is provided with a slit hole 30a into which the protrusion 7c can be entered (be guided). When the protrusion 7c enters the slit hole 30a, the electrical connection end section 7a is locked and gripped by the cylindrical tube member 30. The slit hole 30a has a bent portion 30b that is bent so as to extend in a direction inclined with respect to a circumferential direction C of the cylindrical tube member 30 while extending in a depth direction A of the recessed space for connector insertion 24a. The cylindrical tube member 30 rotates in a circumferential direction C, but is fixed in the processor 20 so as not to move in the depth direction A of the recessed space for connector insertion 24a. Therefore, as illustrated in FIG. 4, since the cylindrical tube member 30 rotates in the circumferential direction C of the cylindrical tube member 30 and thus the protrusion 7c moves in response to the inclination of the slit hole 26a to which the protrusion 7c is locked, the electrical connection end section 7a locked and gripped by the cylindrical tube member 30 moves in the depth direction A of the recessed space for connector insertion 24a. The processor-side electrical connection terminal 28a described above is provided at the back side of the recessed space for connector insertion 24a. Therefore, the guiding mechanism 26 guides the electrical connection end section 7a of the connector 7 to the processor-side electrical connection terminal 28a. The rotation of the cylindrical tube member 30 in the circumferential direction C is performed in conjunction with, for example, the operation of the operation lever 29 to be described later.

In this way, the guiding mechanism 26 is configured to lock, grip, and guide the electrical connection end section 7a of the connector 7 so as to connect the connector-side electrical connection terminal provided in the electrical connection end section 7a inserted into the recessed space for connector insertion 24a to the processor-side electrical connection terminal 28c. It is configured to lock, grip and guide the connection end section 7a.

When the processor 20 includes such a guiding mechanism 26, it is preferable that the lock mechanism 62 be configured to make the shutter 40 into the locked state in conjunction with the operation of the guiding mechanism 26 that guides the electrical connection end section 7a. Specifically, it is preferable that the lock mechanism 62 be configured so that at least a part of the stopper 60 enters the movement path of the shutter 40 in conjunction with the operation of the guiding mechanism 26 that guides the electrical connection end section 7a. As described above, the guiding mechanism 26 has the function of connecting the electrical connection terminal in the electrical connection end section 7a to the processor-side electrical connection terminal 28c, and is operated when the endoscope is connected to the processor 20 and used. If the stopper 60 is configured to enter the movement path of the shutter 40 in conjunction with such an operation, the shutter 40 can be constrained to the closed state in conjunction with the operation that is necessarily operated when the connector 7 is connected to the processor 20, and can reliably prevent the shutter 40 from opening while the connector 7 is connected to the processor 20. As a result, it is possible to reliably prevent the operator's finger from entering the recessed space for connector insertion 24c.

According to one embodiment, the processor 20 includes the operation lever 29 for guiding the electrical connection end section 7a to the connection position with the processor-side electrical connection terminal 28c on the processor side while receiving the electrical connection end section 7a. In this case, it is preferable that the lock mechanism 62 be configured so that at least a part of the stopper 60 enters the movement path of the shutter 40 in conjunction with the operation of the operation lever 29 that guides the electrical connection end section 7a.

Figure 5:
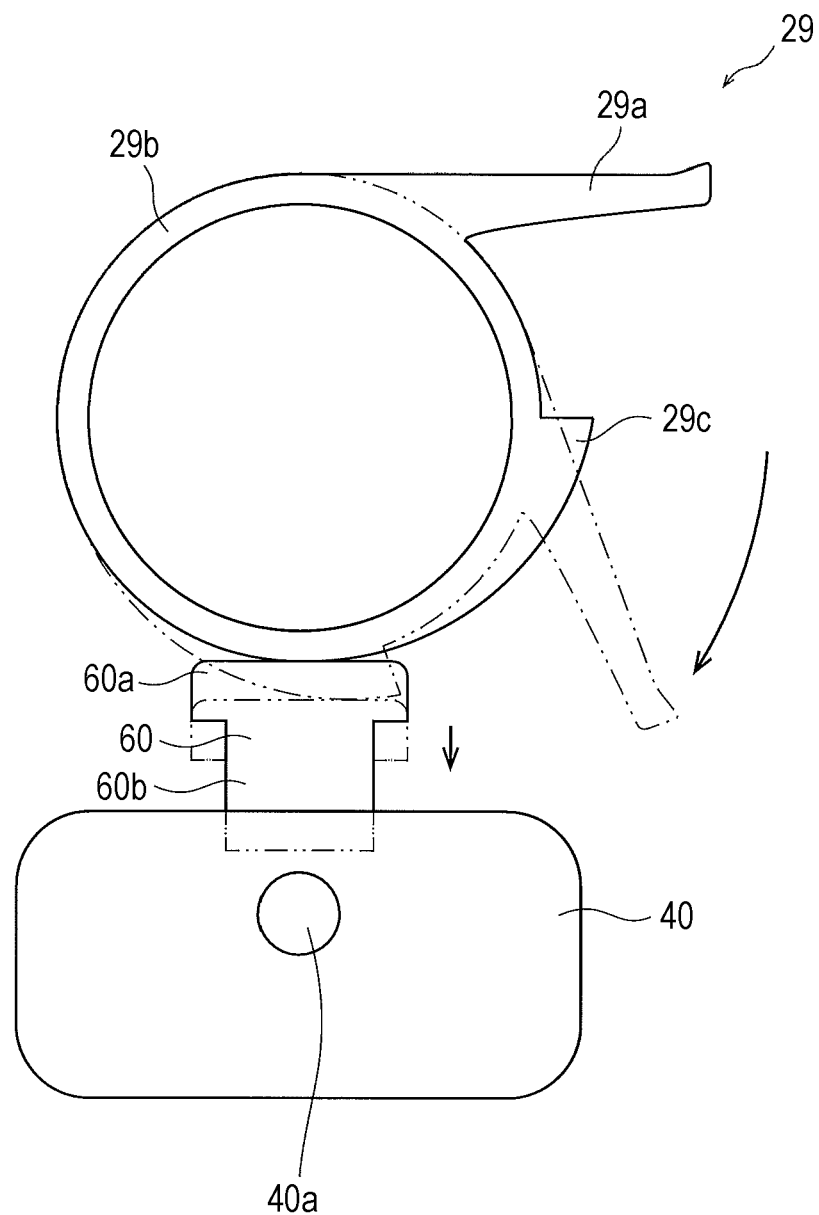
FIG. 5 is a diagram schematically illustrating an example of a shutter, a stopper, and an operation lever according to an embodiment.

Here, the operation lever 29 will be described with reference to FIG. 5. FIG. 5 is a diagram schematically illustrating an example of the shutter 40, the stopper 60, and the operation lever 29. The operation lever 29 is a lever operated by the operator, and as illustrated in FIGS. 2 and 5, a lever 29a extending from the middle of the circumference of the cylindrical tube portion 29b to the outer circumferential side is formed. The operation lever 29 rotates around the center of the cylindrical circle by operating the lever 29a. A thick part 29c in which a radial length (thickness) of the cylindrical tube portion 29b gradually changes to one side in the circumferential direction and becomes larger is provided in a part of the circumferential direction region of the cylindrical tube portion 29b.

In FIG. 5, the operation lever 29 when the connector is not connected to the connector receiving part 22a is illustrated by a solid line, and the operation lever 29 when the connector 7 is connected to the connector receiving part 22a is illustrated by a broken line. When the connector is not connected to the connector receiving part 22a, the operation lever 29 is in contact with an upper end section 60a of the stopper 60 at a position adjacent to the thick part 29c in the circumferential direction. Note that the stopper 60 is urged to move to the operation lever 29 side by the urging member such as a spring. At this time, the lower end section 60b of the stopper 60 is located above the upper end section of the shutter 40. Therefore, the shutter 40 can move to the back side in the recessed space for connector insertion 24c without being blocked by the stopper 60. In this state, in order to connect connector 7 to the connector receiving part 22a, the connector-side electrical connection end section 7a enters the recessed space for connector insertion 24a, and when the operation lever 29 rotates in the direction of the arrow in FIG. 5, the upper end section 60a of the stopper 60 is pushed downward by the thick part 29c of the operation lever 29 and enters the recessed space for connector insertion 24c. Therefore, even if the shutter 40 is applied with an external force, the shutter 40 cannot move to the back side in the recessed space for connector insertion 24c by contacting the lower end section 60b of the stopper 60. In this way, the shutter 40 is constrained to the closed state. At this time, the guiding mechanism 26 guides the endoscope-side electrical connection end section 7a to the connection position with the electrical connection terminal 28a on the processor 20 side in conjunction with the operation of the operation lever 29. Note that the cylindrical tube member 30 of the guiding mechanism 26 is fixed to the cylindrical tube portion 29b of the operation lever 29 so as to integrally rotate with the operation lever 29. The stopper 60 that has entered the movement path of the shutter 40 is configured to be maintained in the state of entering the movement path by friction with the thick part 29c unless the operation lever 29 is operated, whereas a mechanism (not illustrated) for preventing the rotation of the operation lever 29 is operated and thus the stopper 60 may be configured to be maintained in the state of entering the movement path.

If at least a part of the stopper 60 is configured to enter the movement path of the shutter 40 in conjunction with the operation of the operation lever 29, the number of operator's operations performed when connecting the connector 7 to the processor 20 is reduced and the operability is improved. When connecting the connector 7 to the processor 20, the operator often performs the insertion of the connector 7 with one hand while holding a part of the distal tip 5 side of the endoscope with the other hand, so it is preferable that the number of operations be reduced.

On the other hand, if the operation lever 29 is operated to rotate in the opposite direction of when the shutter 40 is closed while the stopper 60 enters the movement path of the shutter 40, the stopper 60 is evacuated from the movement path, and the locked state of shutter 40 is released.

In this way, the stopper 60 can freely enter and exit the movement path of the shutter 40.

When the connector 7 is connected to the connector receiving part 22a, the lower end section 60b of the stopper 60 is located above the gap 40a as illustrated in FIG. 5 not to come into contact with the light incident end section 7b arranged in the recessed space for optical connector insertion 24b through the gap 40a. According to one embodiment, it is preferable that a lower end of the stopper 60 be arranged at a position (for example, position of 10% to 90% of the distance between an upper end of shutter 40 and the gap 40a, from the upper end of the shutter 40) between the upper end of the shutter 40 and the gap 40a. As a result, it is possible to protect the light incident end section 7b from the heat when the stopper 60 is made of resin while reliably preventing the shutter 40 from moving.

A maximum moving distance of the stopper 60 that is pushed down and moves by the thick part 29*c* is preferably shorter than the circumferential length of the thick part 29*c* along the circumferential direction of the cylindrical tube portion 29*b*, as in the example illustrated in FIG. 5. As a result, it is possible to smoothly move the stopper 60, According to one embodiment, the maximum moving distance of the stopper 60 is preferably 5 to 50% and more preferably 10 to 25% of the circumferential length of the thick part 29*c*. As a result, it is possible to reduce the operation amount of the operation lever 29 and reduce the operator's operational burden while ensuring the smooth movement of the stopper 60.

Note that when removing the connector 7 from the connector receiving part 22*a*, if the operation lever 29 rotates in the direction opposite to the arrow in FIG. 5, the stopper 60 moves upward by being applied with the urging force, and the lower end section 60*b* of the stopper 60 comes from the recessed space for connector insertion 24*c*. In the state where the lower end section 60*b* of the stopper 60 moves above the shutter 40, the shutter 40 can move to the back side in the recessed space for connector insertion 24*c* because the movement is not blocked. That is, the shutter 40 is in an openable/closable operation state.

According to one embodiment, when the connector receiving part 22*a* is not used, that is, when the connector receiving part 22*a* does not receive the electrical connection end section 7*a* of the connector 7, it is preferable that the connector receiving part 22*a* be closed by the cover member (not illustrated). The cover member is, for example, a lid made of resin or metal, and is configured to be locked to the operation lever 29.

When the communication and the transmission and reception of power between two connection end sections connected to each other are performed wirelessly, a transparent member for passing light is arranged in the processor-side connection end section, but according to the processor 20 described above, it is possible to prevent the operator's finger from entering the recessed space for connector insertion 24*c* and from touching and contaminating the surface of the member while the connector 7 is connected to the processor 20.

Although the processor for endoscope and the endoscopic system of the present invention have been described in detail, the processor for endoscope and the endoscopic system of the present invention are not limited to the above embodiments, and various improvements and various improvements can be made without departing from the gist of the present invention.

REFERENCE SIGNS LIST

1 Flexible tube
2 Bending tube
3 Operation unit
4 Bending operation lever
5 Distal tip
6 Universal tube
7, 7* Connector
7*a*, 7*a** Electrical connection end section
7*b*, 7*b** Light incident end section
20 Processor
22*a*, 22*c* Connector receiving part
22*b* Optical connector receiving part
24*a*, 24*c* Recessed space for connector insertion
24*b* Recessed space for optical connector insertion
28*a*, 28*c* Electrical connection terminal
28*b* Light emission part
29 Operation lever
29*a* Lever
29*b* Main body part
29*c* Thick part
40 Shutter
42 Shutter mechanism
60 Stopper
60*a* Upper end section
60*b* Lower end section
62 Lock mechanism

The invention claimed is:

1. A processor for endoscope, comprising:
   a first connector receiving part configured to be provided with a first recessed space for receiving a connector-side first connection end section of the connector-side first connection end section and a connector-side second connection end section of an endoscope connector connected to the processor for endoscope, and connect the connector-side first connection end section received in the first recessed space and a processor-side first connection end section of the processor for endoscope;
   a second connector receiving part configured to be provided with a second recessed space different from the first recessed space, and connect the connector-side second connection end section received in the second recessed space and a processor-side second connection end section of the processor for endoscope;
   a shutter mechanism configured to be provided in the second connector receiving part and open a shutter by an external force, the shutter having a gap through which the connector-side second connection end section passes and being configured to partition the second recessed space from the outside; and
   a lock mechanism configured to make the shutter into a locked state constraining the shutter from an openable/closable operation state to a closed state during a period when the connector-side first connection end section and the processor-side first connection end section are connected, and release the locked state of the shutter when the connection between the connector-side first connection end section and the processor-side first connection end section is released.

2. The processor for endoscope according to claim 1, wherein
   the shutter is configured to be opened to the outside by moving in the second recessed space, and
   the lock mechanism has a stopper of which at least a part freely enters and exits a path in the second recessed space in which the shutter moves, and is configured so that the at least a part of the stopper enters the path to prevent the shutter from moving.

3. The processor for endoscope according to claim 2, further comprising:
   a guiding mechanism configured to guide the connector-side first connection end section to a connection position with the processor-side first connection end section while receiving the connector-side first connection end section, wherein
   the lock mechanism is configured so that the at least a part of the stopper enters the path in conjunction with an operation of the guiding mechanism that guides the connector-side first connection end section.

4. The processor for endoscope according to claim 2, further comprising:
   an operation lever configured to guide the connector-side first connection end section to the connection position with the processor-side first connection end section while receiving the connector-side first connection end section, wherein the lock mechanism is configured so that the at least a part of the stopper enters the path in conjunction with an operation of the operation lever that guides the connector-side first connection end section.

5. The processor for endoscope according to claim 1, further comprising:

a guiding mechanism configured to guide the connector-side first connection end section to a connection position with the processor-side first connection end section while receiving the connector-side first connection end section, wherein the lock mechanism is configured so that the shutter is in the locked state in conjunction with an operation of the guiding mechanism that guides the connector-side first connection end section.

6. The processor for endoscope according to claim 1, wherein the second connector receiving part is configured to connect the connector-side second connection end section and the processor-side second connection end section so as to enable transmission and reception of light, and the transmission and reception of light is performed by spatial transmission via an optical path in a space between the connector-side second connection end section and the processor-side second connection end section.

7. The processor for endoscope according to claim 1, wherein the first connector receiving part is configured to connect the connector-side first connection end section and the processor-side first connection end section so as to enable communication and transmission and reception of power, and the communication and the transmission and reception of power are performed by the spatial transmission of light via the optical path in the space between the connector-side first connection end section and the processor-side first connection end section.

8. An endoscopic system, comprising:

the processor for endoscope according to claim 1; and an endoscope having the endoscope connector.

9. The endoscopic system according to claim 8, wherein when the endoscope connector is referred to as a first connector and the connector-side first connection end section is referred to as a first connector-side first connection end section, the second connector receiving part is configured to receive a second connector-side first connection end section of a second connector mounted on the second connector receiving part and different from the first connector in the second recessed space, and connect the received second connector-side first connection end section and a processor-side third connection end section of the processor for endoscope.

10. The endoscopic system according to claim 9, wherein the recessed spaces, that receive a light incident end section, of each of the first connector and the second connector commonly including the light incident end section as the connector-side second connection end section, the light incident end section receiving incidence of light from the processor for endoscope, is provided in the second recessed space.

11. An endoscopic system, comprising:

the processor for endoscope according to claim 1; and an endoscope having a second connector mounted on the second connector receiving part and different from the first connector when the endoscope connector is referred to as a first connector.

12. The endoscopic system according to claim 11, wherein the second connector receiving part is configured to receive the second connector-side first connection end section of the second connector in the second recessed space and connect the received second connector-side first connection end section and a processor-side third connection end section of the processor for endoscope.

* * * * *